(12) United States Patent
Speronello et al.

(10) Patent No.: US 7,323,138 B2
(45) Date of Patent: Jan. 29, 2008

(54) METHOD FOR EXTENDING THE STORAGE LIFE OF AN ARTICLE

(76) Inventors: Barry K. Speronello, 15 Carriage Trail, Belle Meade, NJ (US) 08502; Dennis Sekutowski, One Edna Horn Dr., Stockton, NJ (US) 08859; Richard P. Hannan, 639 Rosemont Ringoes Rd., Stockton, NJ (US) 08559

(*) Notice: Subject to any disclaimer, the term of this patent is extended or adjusted under 35 U.S.C. 154(b) by 652 days.

(21) Appl. No.: 10/699,040

(22) Filed: Oct. 31, 2003

(65) Prior Publication Data

US 2005/0095170 A1  May 5, 2005

(51) Int. Cl.
*A61L 2/00*  (2006.01)
(52) U.S. Cl. .............................. 422/28; 422/1; 422/37
(58) Field of Classification Search ................. 422/1, 422/28, 37
See application file for complete search history.

(56) References Cited

U.S. PATENT DOCUMENTS

| | | | | |
|---|---|---|---|---|
| 5,974,810 | A | * 11/1999 | Speronello | .................. 62/66 |
| 6,294,108 | B1 | 9/2001 | Speronello et al. | .... 252/187.21 |
| 2005/0019210 | A1 * | 1/2005 | Rosenblatt et al. | ........... 422/37 |
| 2005/0048174 | A1 * | 3/2005 | Marckini et al. | ........... 426/321 |

* cited by examiner

*Primary Examiner*—Krisanne Jastrzab
(74) *Attorney, Agent, or Firm*—Raymond F. Keller; Brian W. Stegman

(57) ABSTRACT

A method for treating an article which involves exposing an article within a space to a concentration of chlorine dioxide gas that exceeds the IDLH, STEL or TLV, then reducing the concentration of chlorine dioxide gas within the space to a positive quantity below the IDLH, STEL or TVL. Thereafter, additional chlorine dioxide gas is introduced into the space, but the concentration within the space remains below the IDLH, STEL or TVL.

18 Claims, No Drawings

METHOD FOR EXTENDING THE STORAGE LIFE OF AN ARTICLE

FIELD OF THE INVENTION

This invention relates to a method for extending the storage life of an article with chlorine dioxide gas.

BACKGROUND OF THE INVENTION

Chlorine dioxide, or $ClO_2$ is a well known biocide that has been discussed as an agent to extend the storage life of goods. An efficient way to apply $ClO_2$ gas and to treat such goods is to use it to fumigate the goods in the areas in which they are stored and/or transported. Examples of such areas include shipping containers on ocean transport vessels, freight holds of ocean transport vessels, the trailer section of motor freight trucks, and various warehouse enclosures. However, it can be dangerous to treat such spaces with $ClO_2$ gas due to the inhalation toxicity of $ClO_2$. Illness or death can result if a human enters the treated space when the $ClO_2$ gas concentration is above safe levels.

SUMMARY OF THE INVENTION

Generally, this invention provides a method for treating an article with chlorine dioxide to increase storage life while minimizing the hazard of inhalation toxicity to humans. The method comprises treating an article within a space, preferably a harvested agricultural product, wherein the article is exposed to a concentration of $ClO_2$ gas within the space equal to or exceeding that which is considered immediately dangerous to life and health (IDLH), preferably equal to or exceeding the Short Term Exposure Limit (STEL), and more preferably equal to or exceeding the Threshold Limit Value (TLV). The IDLH concentration is the concentration at which exposure to a chemical can result in serious health consequences, and is currently defined by the US National Institute of Occupational Safety and Health (NIOSH) as 5 volume ppm in air. The STEL is the maximum average concentration allowed for inhalation exposure over 15 minutes, and is currently defined by several regulatory organizations, including the American Congress of Government Industrial Hygienists (ACGIH), the US Occupational Safety and Health Administration (OSHA), and NIOSH as 0.3 ppm. The TLV is the maximum average concentration allowed for inhalation exposure for 8 hours, and is defined by the currently defined by the ACGIH as 0.1 ppm. Over time, both the names for these standards and the values may change as regulations evolve and knowledge improves. The hazard classes, however, are expected to remain in place.

The concentration of $ClO_2$ gas in air may be measured by OSHA standard method ID-202 or an equivalent method.

The concentration of $ClO_2$ gas within the space is then reduced to a positive concentration less than IDLH, preferably less than the STEL, and more preferably less than the TLV. Additional $ClO_2$ is then introduced into the space without the concentration of $ClO_2$ exceeding the IDLH, preferably not exceeding the STEL, and more preferably not exceeding the TLV.

DETAILED DESCRIPTION OF THE PREFERRED EMBODIMENTS

The invention relates to a method of extending the storage life of an article through treatment with chlorine dioxide gas. The method effectively extends the storage life of the goods while limiting the potential for human injury from inhalation of chlorine dioxide gas.

The article treated in the method of the invention may be any item that can have its storage life extended by exposure to chlorine dioxide gas. Extension of storage life for purposes of the invention shall mean any inhibition of rot, decay, disease or other degradation that can affect the article, including but not limited to the elimination, reduction in number, or reduction in the rate of proliferation of article-degrading microorganisms. Preferably, the article comprises a harvested agricultural product.

The method involves exposing an article within a space to a concentration of chlorine dioxide gas that exceeds the IDLH, STEL or TLV, then reducing the concentration of chlorine dioxide gas within the space to below the IDLH, STEL or TVL, but above zero. Thereafter, additional chlorine dioxide gas is introduced into the space, but the concentration remains below the IDLH, STEL or TVL. Presently, the IDLH, STEL, and TLV are, respectively, 10 ppm, 0.3 ppm, and 0.1 ppm (all by volume).

Any technique or techniques for generating the chlorine dioxide gas and exposing the goods to the chlorine dioxide gas may be used, so long as it may be utilized to create the concentrations required in the invention. Preferred examples of $ClO_2$-producing materials are described in U.S. Pat. No. 6,294,108, which is incorporated herein by reference.

Reduction of the chlorine dioxide concentration to a positive quantity below the IDLH, STEL or TLV threshold may be accomplished by active dilution or evacuation of the chlorine dioxide gas within the space, or passive dissipation of the chlorine dioxide gas from or within the space. Chlorine dioxide may continue to be introduced to the space during the reduction step, so long as the concentration of chlorine dioxide within the space ebbs to a level below IDLH, STEL or TLV.

After the reduction step, additional chlorine dioxide gas is introduced to the space containing the article, but the concentration of chlorine dioxide gas does not exceed IDLH, STEL or TLV. It is believed that this low-concentration chlorine dioxide exposure after an initial high-concentration exposure effectively extends storage life without the health risks associated with high chlorine dioxide concentrations.

What is claimed is:

1. A method of treating an article, comprising:
   (a) exposing the article within a space to a concentration of chlorine dioxide of at least 5 ppm; then
   (b) using active dilution to reduce the concentration of chlorine dioxide gas within the space to a positive quantity less than 5 ppm; then
   (c) introducing additional chlorine dioxide gas into the space such that the concentration of chlorine dioxide gas into the space such that the concentration of chlorine dixoxide gas within the space remains below 5 ppm.

2. A method of treating an article, comprising:
   (a) exposing the article within a space to a concentration of chlorine dioxide of at least 0.3 ppm; then
   (b) using active dilution to reduce the concentration of chlorine dioxide gas within the space to a positive quantity less than 0.3 ppm; then
   (c) introducing additional chlorine dioxide gas into the space such that the concentration of chlorine dioxide gas into the space such that the concentration of chlorine dixoxide gas within the space remains below 0.3 ppm.

3. A method of treating an article, comprising:
(a) exposing the article within a space to a concentration of chlorine dioxide of at least 0.1 ppm; then
(b) using active dilution to reduce the concentration of chlorine dioxide gas within the space to a positive quantity less than 0.1 ppm; then
(c) introducing additional chlorine dioxide gas into the space such that the concentration of chlorine dioxide gas into the space such that the concentration of chlorine dixoxide gas within the space remains below 0.1 ppm.

4. A method of treating an article, comprising:
(a) exposing the article within a space to a concentration of chlorine dioxide of at least 5 ppm; then the IDLH; then
(b) using active dilution to reduce the concentration of chlorine dioxide gas within the space to a positive quantity less than the IDLH; then
(c) introducing additional chlorine dioxide gas into the space such that the concentration of chlorine dioxide gas into the space such that the concentration of chlorine dixoxide gas within the space remains below the IDLH.

5. A method of treating an article, comprising:
(a) exposing the article within a space to a concentration of chlorine dioxide of at least 5 ppm; then the STEL; then
(b) using active dilution to reduce the concentration of chlorine dioxide gas within the space to a positive quantity less than the STEL; then
(c) introducing additional chlorine dioxide gas into the space such that the concentration of chlorine dioxide gas into the space such that the concentration of chlorine dixoxide gas within the space remains below the STEL.

6. A method of treating an article, comprising:
(a) exposing the article within a space to a concentration of chlorine dioxide of at least 5 ppm; then the TLV; then
(b) using active dilution to reduce the concentration of chlorine dioxide gas within the space to a positive quantity less than the TLV; then
(c) introducing additional chlorine dioxide gas into the space such that the concentration of chlorine dioxide gas into the space such that the concentration of chlorine dixoxide gas within the space remains below the TLV.

7. The method of claim 1, wherein the article is a harvested agricultural product.

8. The method of claim 2, wherein the article is a harvested agricultural product.

9. The method of claim 3, wherein the article is a harvested agricultural product.

10. The method of claim 4, wherein the article is a harvested agricultural product.

11. The method of claim 5, wherein the article is a harvested agricultural product.

12. The method of claim 6, wherein the article is a harvested agricultural product.

13. The method of claim 1 further comprising generating chlorine dioxide gas by exposing a composition consisting essentially of at least one dry metal chlorite and at least one dry solid hydrophilic material comprising at least one inorganic material selected from the group consisting of hydrous clays, calcined clays, acidified clays and acidified calcined clays, wherein said composition is one which passes both the Dry Air and Humid Air Tests, to air comprising water vapor.

14. The method of claim 2 further comprising generating chlorine dioxide gas by exposing a composition consisting essentially of at least one dry metal chlorite and at least one dry solid hydrophilic material comprising at least one inorganic material selected from the group consisting of hydrous clays, calcined clays, acidified clays and acidified calcined clays, wherein said composition is one which passes both the Dry Air and Humid Air Tests, to air comprising water vapor.

15. The method of claim 3 further comprising generating chlorine dioxide gas by exposing a composition consisting essentially of at least one dry metal chlorite and at least one dry solid hydrophilic material comprising at least one inorganic material selected from the group consisting of hydrous clays, calcined clays, acidified clays and acidified calcined clays, wherein said composition is one which passes both the Dry Air and Humid Air Tests, to air comprising water vapor.

16. The method of claim 4 further comprising generating chlorine dioxide gas by exposing a composition consisting essentially of at least one dry metal chlorite and at least one dry solid hydrophilic material comprising at least one inorganic material selected from the group consisting of hydrous clays, calcined clays, acidified clays and acidified calcined clays, wherein said composition is one which passes both the Dry Air and Humid Air Tests, to air comprising water vapor.

17. The method of claim 5 further comprising generating chlorine dioxide gas by exposing a composition consisting essentially of at least one dry metal chlorite and at least one dry solid hydrophilic material comprising at least one inorganic material selected from the group consisting of hydrous clays, calcined clays, acidified clays and acidified calcined clays, wherein said composition is one which passes both the Dry Air and Humid Air Tests, to air comprising water vapor.

18. The method of claim 6 further comprising generating chlorine dioxide gas by exposing a composition consisting essentially of at least one dry metal chlorite and at least one dry solid hydrophilic material comprising at least one inorganic material selected from the group consisting of hydrous clays, calcined clays, acidified clays and acidified calcined clays, wherein said composition is one which passes both the Dry Air and Humid Air Tests, to air comprising water vapor.

* * * * *